(12) United States Patent
Gandianco et al.

(10) Patent No.: US 6,231,582 B1
(45) Date of Patent: *May 15, 2001

(54) CORNEAL POCKETING TOOL

(75) Inventors: Isidro Gandianco, Fremont; John A. Scholl, Danville, both of CA (US)

(73) Assignee: KeraVision, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/993,445

(22) Filed: Dec. 18, 1997

(51) Int. Cl.[7] .......................................................... A61F 9/00
(52) U.S. Cl. ............................................................ 606/166
(58) Field of Search .................................. 606/166, 107, 606/167

(56) References Cited

U.S. PATENT DOCUMENTS

| | | |
|---|---|---|
| 4,452,235 | 6/1984 | Reynolds . |
| 4,573,998 | 3/1986 | Mazzocco . |
| 4,655,774 | 4/1987 | Choyce . |
| 4,671,276 | 6/1987 | Reynolds . |
| 4,766,895 | 8/1988 | Reynolds . |
| 4,961,744 | 10/1990 | Kilmer et al. . |
| 5,090,955 | 2/1992 | Simon . |
| 5,163,934 | 11/1992 | Munnerlyn . |
| 5,222,967 | 6/1993 | Rae et al. . |
| 5,372,580 | 12/1994 | Simon et al. . |
| 5,405,355 | 4/1995 | Peyman et al. . |
| 5,411,510 * | 5/1995 | Fugo ..................................... 606/166 |
| 5,547,468 | 8/1996 | Simon et al. . |
| 5,607,437 | 3/1997 | Simon et al. . |
| 5,653,725 * | 8/1997 | Simon et al. ........................ 606/166 |

FOREIGN PATENT DOCUMENTS

| | | |
|---|---|---|
| WO 95/17144 | 6/1995 | (WO) . |
| WO 97/04726 | 2/1997 | (WO) . |
| WO 98/46192 | 10/1998 | (WO) . |

OTHER PUBLICATIONS

Temirov et al. "Refractive circular tunnel keratoplasty in the correction of high myopia" *Vestnik Oftamologii* (1991) 3:21–31.

* cited by examiner

Primary Examiner—Michael Buiz
Assistant Examiner—(Jackie) Tan-Uyenn T. Ho
(74) Attorney, Agent, or Firm—Harry Macey; KeraVision, Inc.

(57) ABSTRACT

The invention relates to a corneal pocketing tool for separating the lamella of the cornea. The corneal pocketing tool has a dissector portion for insertion into a corneal incision and a reference surface or region adapted to contact the cornea. As the dissector is advanced into the corneal incision the reference region comes into contact with the surface of the cornea and resists further advancement of the dissector. As the reference region is moved in a clockwise or counterclockwise direction, the dissector portion follows in the same direction forming a pocket in the cornea.

23 Claims, 5 Drawing Sheets

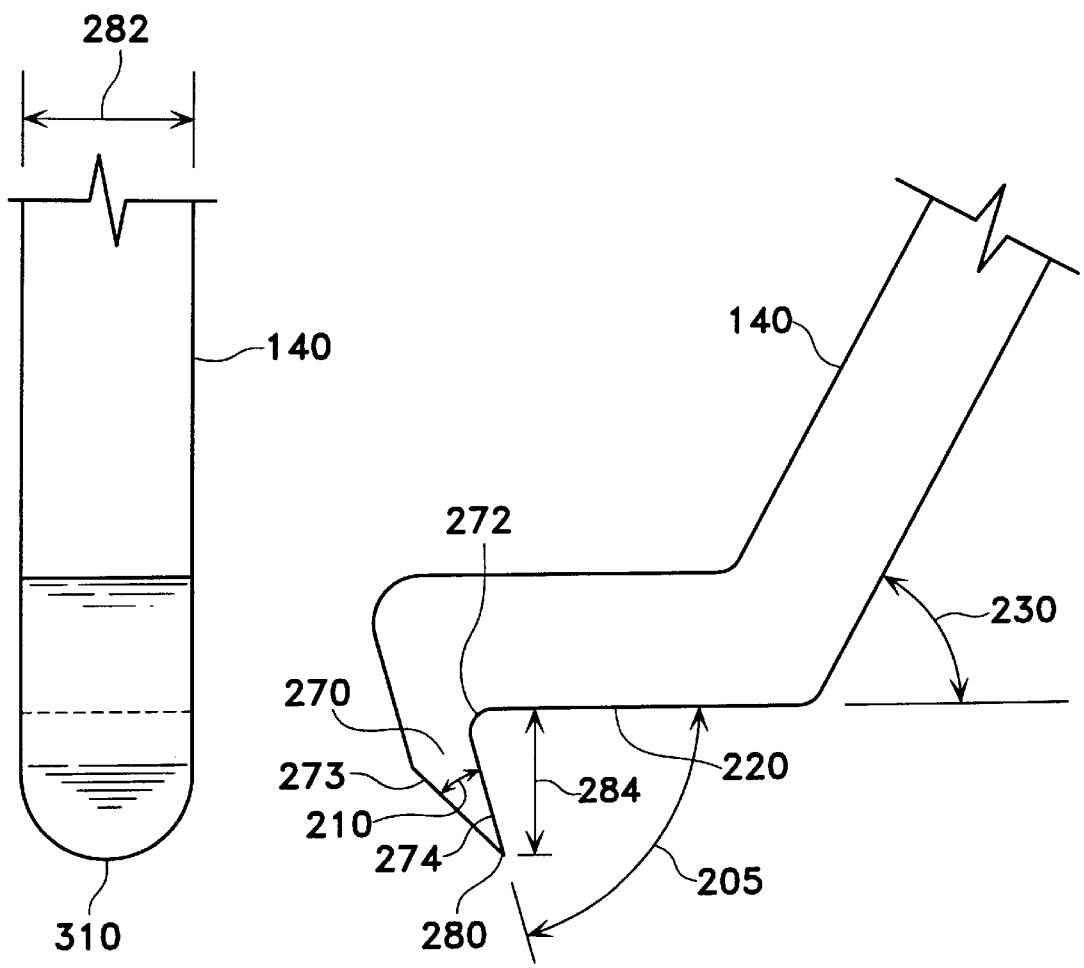

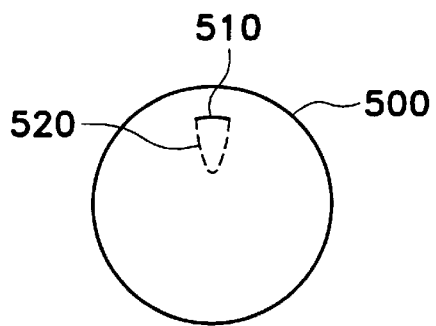
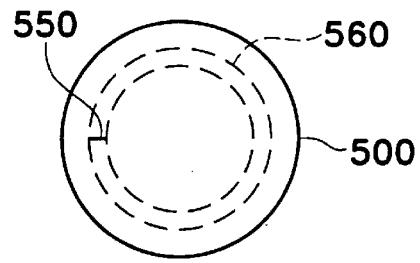
FIG. 7   FIG. 8
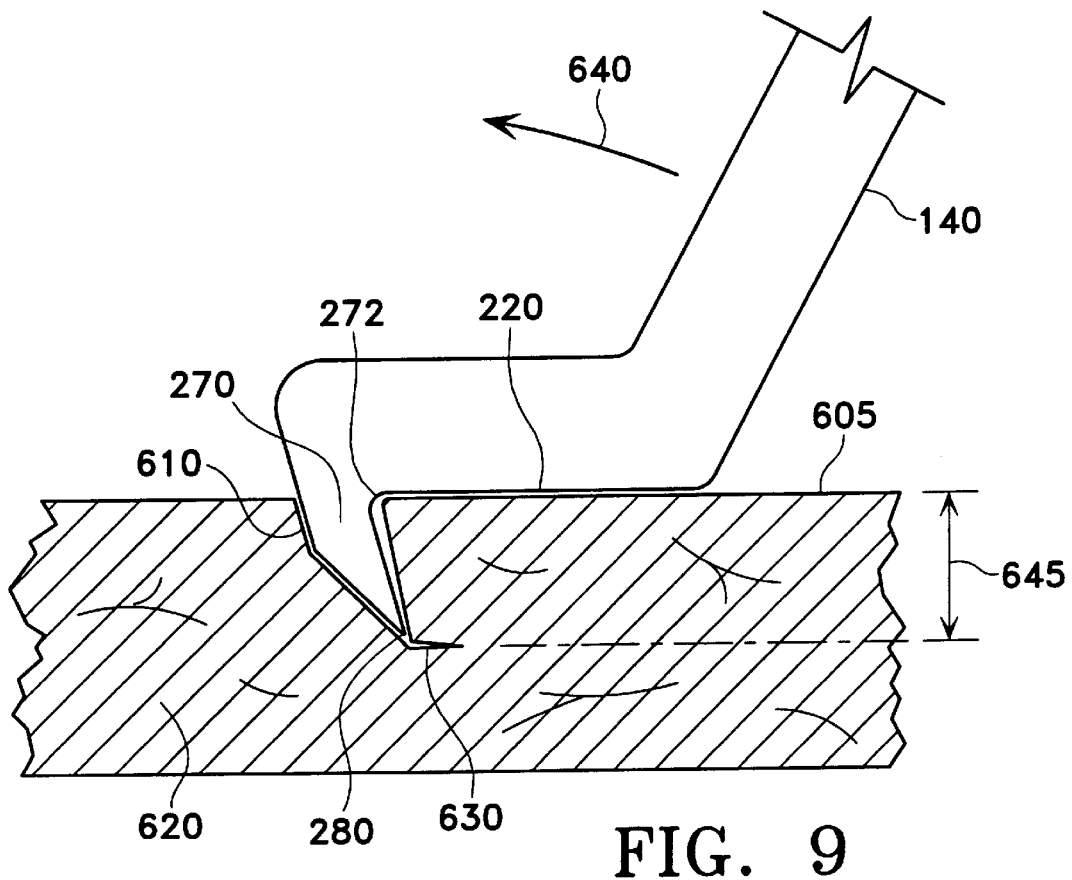
FIG. 9

CORNEAL POCKETING TOOL

FIELD OF THE INVENTION

This invention involves a surgical instrument for intracorneal pocketing. The handheld surgical tool is typically inserted into a corneal incision and maneuvered to create a corneal pocket. This invention also provides a method for creating an intracorneal pocket.

BACKGROUND OF THE INVENTION

Anomalies of the overall shape of the eye often cause appreciable visual disorders, such as hyperopia, myopia, and astigmatism. The surgical treatment of these and other disorders often involve creating a separation or pocket between the stromal layers of the cornea. Various materials, substances, or inserts may be placed within the pocket to effectuate changes in the geometry of the cornea or deliver drugs or other biologic agents.

For example, these disorders may be corrected using surgical methods involving the implantation of polymeric rings (intrastromal corneal rings) in the eye's corneal stroma to change the curvature of the cornea. Previous work involving the implantation of polymethylmethacrylate rings, allograft corneal tissue, and hydrogels is well documented. One of the ring devices involves a split ring design which is inserted into a pocket in the form of an annular channel dissected in the stromal layer of the cornea. See, for instance, the use of intrastromal rings in U.S. Pat. Nos. 4,452,235 to Reynolds; 4,671,276 to Reynolds; 4,766,895 to Reynolds; and 4,961,744 to Kilmer et al. Temirov et al., "Refractive circular tunnel keroplasty in the correction of high myopia", Vestnik Oftalmologii Mar. 21–31, 1991 suggests the use of collagen thread as intrastromal corneal ring material.

It is also known to use arcuate channels containing a gel-based insert centered on the cornea to correct certain visual disorders. U.S. Pat. Nos. 5,090,955 and 5,372,580, to Simon, suggest introducing a settable polymer or gel into an intrastromal channel and allowing the polymer to set.

These types of procedures typically involve making a partial depth incision into the cornea, either radial or circumferential, and then separating the lamella at a known depth. The separation may be continued or furthered, using a variety of instruments as necessary, until the desired channel or pocket is formed at the desired depth below the surface of the cornea. In U.S. Pat. No. 5,547,468 to Simon et al., for example, once the incision has been formed, a blunt spatula is inserted through the incision to separate the lamella. Following this initial separation of lamella with the blunt spatula, a channel starting instrument is inserted into the incision and then rotated in a manner such that the lamella is separated along an arcuate path.

Creation of the initial separation using an ordinary blunt spatula is often very difficult. There is little visual access to the tip of the instrument at the base of the incision and it may be difficult for the surgeon to feel the bottom of the incision. Improper placement or inadequate manipulation of the instrument by the surgeon may result in an initial separation at the wrong depth relative to the surface of the cornea or no separation at all. Excessive manipulation of the spatula in attempting to initiate the separation at the base of the incision may result in damage or trauma to the incised tissue as well as the tissue below the incision.

There is a need therefor for a pocketing tool constructed to provide a reliable lamella separation at the desired depth below the surface of the cornea which is less sensitive to manipulation difficulties inherent in prior art instruments.

SUMMARY OF THE INVENTION

This invention is a surgical instrument for separating the lamella of a cornea. The instrument has a dissector and a reference region adapted to contact the surface of the cornea. In one aspect of the present invention, the dissector is disposed at an angle relative to said reference region of between about 30° and about 150°, preferably less than about 110°.

The reference region may comprise a planar surface or a curved surface. If the reference region is configured to have a curved surface, it will typically have a radius of curvature in the range of about 6 mm to about 10 mm.

As the dissector is inserted into the incision, the free advancement of the dissector is prevented once the reference surface comes into contact against the surface of the cornea.

The reference region and the dissector, being disposed in an angular relation to one another, converge at an intersection. The instrument handle may then be manipulated to cause the dissector to rotate about a point near the intersection. The intersection of the reference region and the dissector may take the form of a radius or radiused surface. The radius in conjunction with the reference region provide a suitable pivot about which the dissector may be rotated to initiate the desired separation at the dissector tip.

The present invention also involves a method of creating an intrastromal separation or pocket at the base of a partial-depth corneal incision involving inserting an instrument having a reference surface in angular relation to a dissector until the reference surface contacts the surface of the cornea and rotating the instrument about the vertex of the intersection of the reference region and the dissector.

The above is a brief description of some deficiencies in the prior art and advantages of the present invention. Other features, advantages, and embodiments of the invention will be apparent to those skilled in the art from the following description, accompanying drawings and appended claims.

BRIEF DESCRIPTION OF THE DRAWINGS

FIG. 4 is a detailed view of the tip section of the pocketing tool of FIG. 1.

FIG. 5 is a side view of the tip section of FIG. 4.

FIGS. 7 and 8 illustrate circumferential and radial incisions respectively.

FIG. 9 illustrates the use of a pocketing tool according to the principles of the present invention.

DESCRIPTION OF THE INVENTION

Prior to explaining the details of the inventive devices, a short explanation of the physiology of the eye is needed to appreciate the functional relationship of these intracorneal inserts or segments to the eye.

Figure 1:
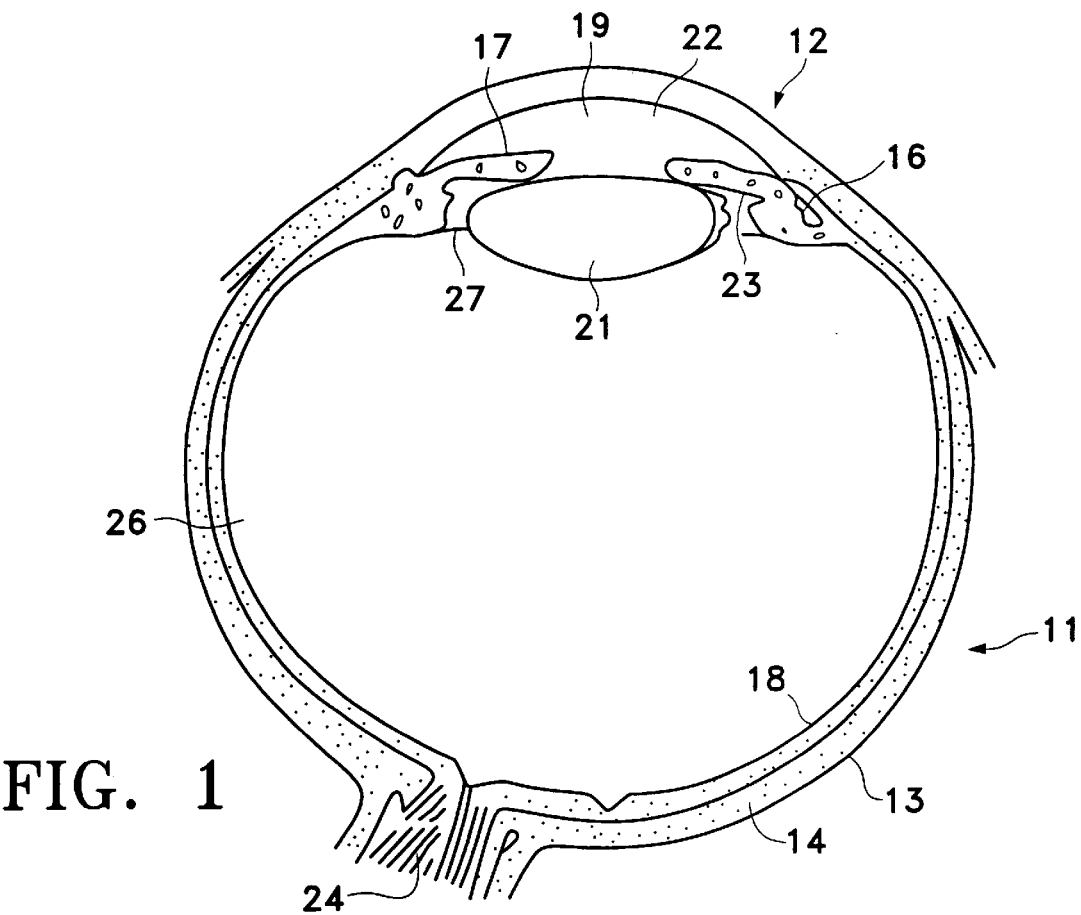
FIG. 1 is a schematic illustration of a horizontal section of the eye.

FIG. 1 shows a horizontal cross-section of the eye with the globe (11) of the eye resembling a sphere with an anterior bulged spherical portion representing the cornea (12).

The globe (11) of the eye consists of three concentric coverings enclosing the various transparent media through which the light must pass before reaching the light-sensitive retina (18). The outermost covering is a fibrous protective portion the posterior five-sixths of which is white and opaque and called the sclera (13), and sometimes referred to as the white of the eye where visible to the front. The anterior one-sixth of this outer layer is the transparent cornea (12).

A middle covering is mainly vascular and nutritive in function and is made up of the choroid, ciliary body (16), and iris (17). The choroid generally functions to maintain the retina (18). The ciliary body (16) is involved in suspending the lens (21) and accommodation of the lens. The iris (17) is the most anterior portion of the middle covering of the eye and is arranged in a frontal plane. It is a thin circular disc similar in function to the diaphragm of a camera, and is perforate near its center by a circular aperture called the pupil (19). The size of the pupil varies to regulate the amount of light which reaches the retina (18). It contracts also to accommodation, which serves to sharpen the focus by diminishing spherical aberration. The iris divides the space between the cornea (12) and the lens (21) into an anterior chamber (22) and the posterior chamber (23). The innermost portion of covering is the retina (18), consisting of nerve elements which form the true receptive portion for visual impressions.

The retina (18) is a part of the brain arising as an outgrowth from the fore-brain, with the optic nerve (24) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (26) is a transparent gelatinous mass which fills the posterior four-fifths of the globe (11). At its sides it supports the ciliary body (16) and the retina (18). A frontal saucer-shaped depression houses the lens.

The lens (21) of the eye is a transparent bi-convex body of crystalline appearance placed between the iris (17) and vitreous body (26). Its axial diameter varies markedly with accommodation. A ciliary zonule (27), consisting of transparent fibers passing between the ciliary body (16) and lens (21) serves to hold the lens (21) in position and enables the ciliary muscle to act on it.

Referring again to the cornea (12), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
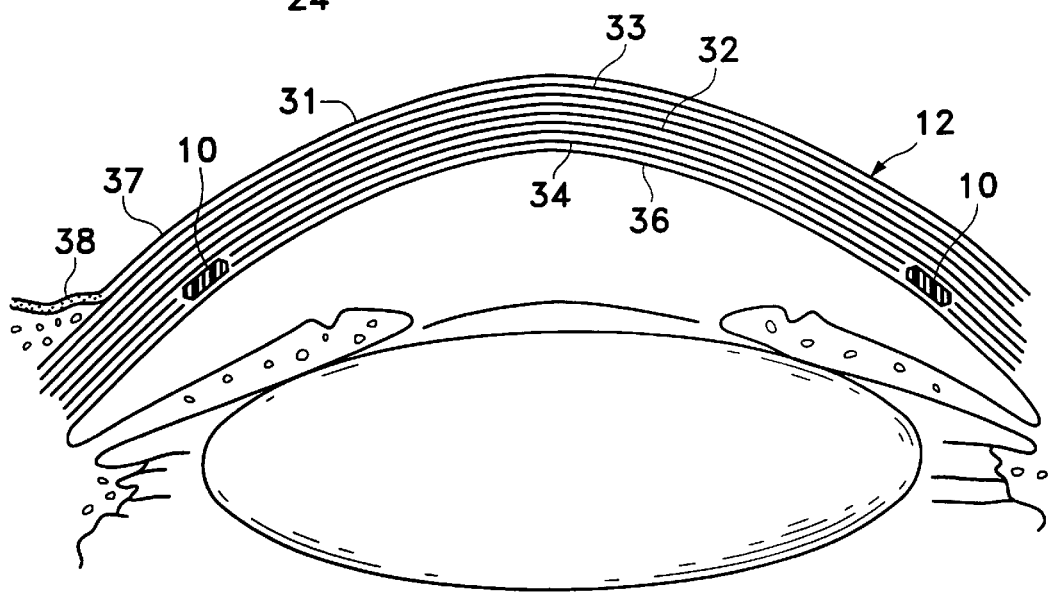
FIG. 2 is a schematic illustration of the anterior portion of the eye showing the various layers of the cornea.

FIG. 2 is a more detailed drawing of the anterior portion of the globe showing the various layers of the cornea (12) making up the epithelium (31). Epithelial cells on the surface thereof function to maintain transparency of the cornea (12). These epithelial cells are rich in glycogen, enzymes and acetylcholine and their activity regulates the corneal corpuscles and controls the transport of water and electrolytes through the lamellae of the stroma (32) of the cornea (12).

An anterior limiting lamella (33), referred to as Bowman's membrane or layer, is positioned between the epithelium (31) and the stroma (32) of the cornea. The corneal stroma (32) are made up of lamellae having bands of fibrils parallel to each other and crossing the whole of the cornea. While most of the fibrous bands are parallel to the surface, some are oblique, especially anteriorly. A posterior limiting lamella (34) is referred to as Descemet's membrane. It is a strong membrane sharply defined from the stroma (32) and resistant to pathological processes of the cornea. The endothelium (36) is the most posterior layer of the cornea and consists of a single layer of cells. The limbus (37) is the transition zone between the conjunctiva (38) and sclera on the one hand and the cornea (12) on the other.

With that background in place, our invention centers on a pocketing tool constructed to form an intrastromal separation at a desired depth below the surface of the cornea. The pocketing tool has a dissecting or delaminating tip and preferably includes an insertion stop feature positioned at a predetermined distance from the tip. As the tip of the pocketing tool is inserted vertically into the incision, the stop feature contacts the outer surface of the cornea and effectively inhibits further advancement of the pocketing tool tip. With the depth of the delaminating tip controlled by the stop feature, the pocketing tool may then be manipulated to accurately create the desired separation.

The stop feature may also provide a steady reference against the surface of the cornea from which the pocketing tool may be rotated. Rotating the pocketing tool about such a reference provides an enhanced measure of control at the delaminating tip as it separates the lamella to form an initial separation or pocket. The pocketing tool is typically provided with an elongated handle positioned relative to the tip to provide the surgeon with optimum visual access and a steady grip and control as the instrument is manipulated.

Figure 3:
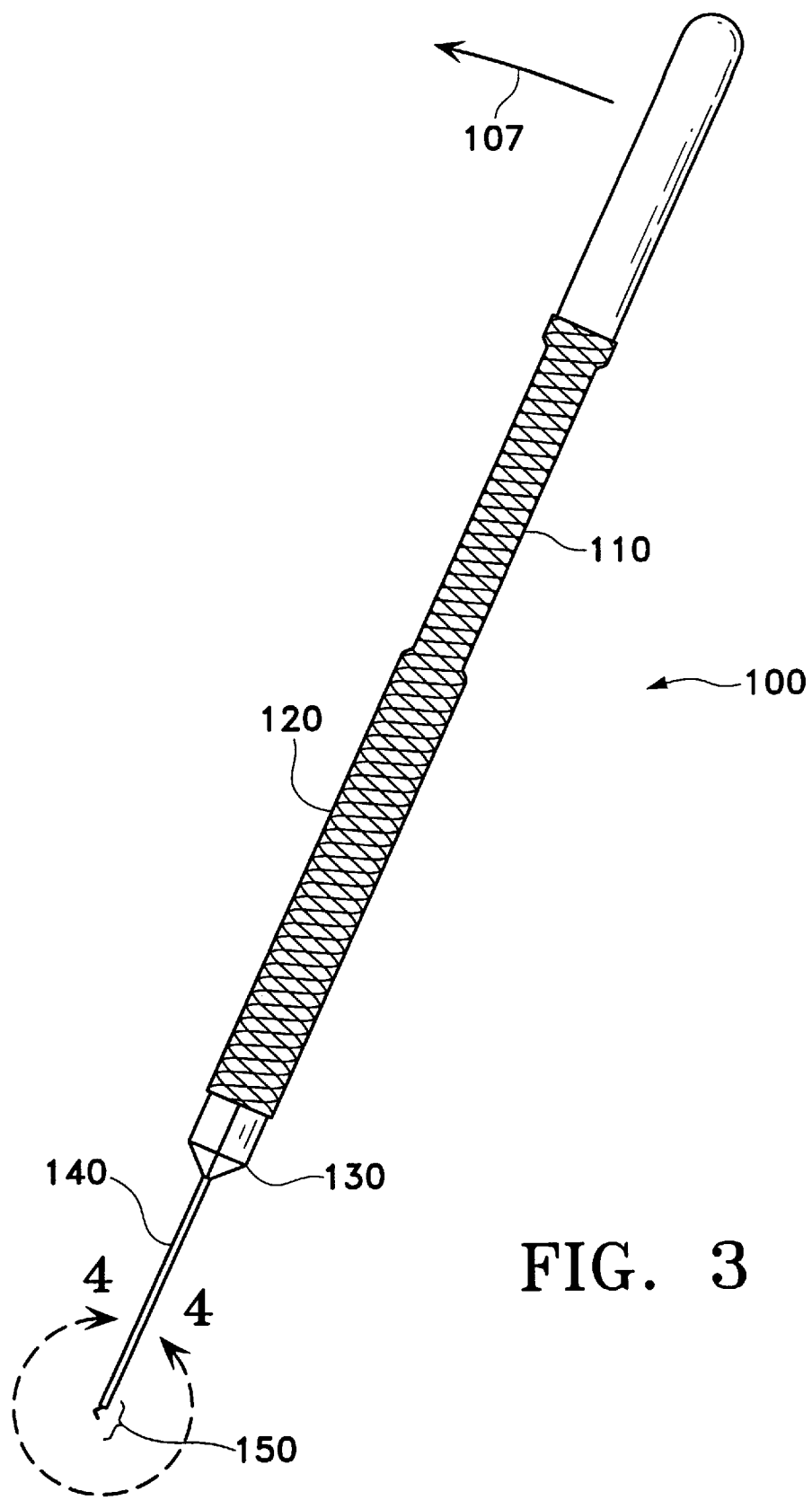
FIG. 3 is a front view of the pocketing tool constructed according to the principles of the present invention.

FIG. 3 illustrates a pocketing tool constructed according to the principles of the present invention. The pocketing tool (100) has an instrument handle (120) and a thin instrument shaft (140) terminating distally in tip section (150). Instrument handle (120) is typically knurled or coated for purposes of gripping, and may have a flat region (110) to allow the instrument to be marked with any desired identifying data.

The shaft (140) connects to the handle (120) at connecting hub (130). Connecting hub (130) securely attaches the proximal end of the shaft (140) to the handle (120). The entire corneal pocketing tool may be of a single piece of material and ground to the final net shape. Alternatively, the shaft (140) may be a separate piece and attached by way of an interference fit with mating features in the hub, or by bonding or welding or the like. The connecting hub (130) may optionally be in the form of a collect or other clamping mechanism that allows substitution of different tip instruments, such as, for example, right and left handed offset handle pocketing tools as described in detail below.

The tip section (150) can be seen more clearly in the magnified front and side views illustrated in FIGS. 4 and 5 respectively. Tip section (150) is constructed to have a reference region (220), which is constructed to contact the surface of the cornea during use, and is connected proximally to the shaft (140) and distally to a dissector (270). The reference region (220) may be a generally flat reference surface, may be curved to match the contour of the cornea, or may have any other features or construction which allows the pocketing tool to reference against the surface of the cornea. If the tip section is constructed of wire material, the reference region may be the outside surface of the wire itself.

The shaft (140) is shown disposed at an angle (230) to the plane of the reference region (220). In practice, the angle (230) is constructed to provide the surgeon with the optimum manual control and visibility for the particular surgery which is to be performed. The angle (230) is typically between about 10° to 170°, preferably between about 30° to about 90°, most preferably about 60°. A small radius (272) may be provided at the transition between the reference region (220) and the dissector (270). Radius (272) may be from about 0.01 to about 0.05 inches.

The dissector may have a variety of constructions including a relatively thin wire construction or may have a flat profile construction as shown. In FIGS. 4 and 5, the dissector (270) has an inner surface (274) and an outer surface (273), and is also disposed in angular relation to the reference region (220). The dissector angle (205), shown as the angle between the inner surface (274) and reference region (220), is typically less than 150°, preferably less than 110°, but may be between about 30° and about 150°, more preferably between about 60° to about 100°, most preferably about 75° as shown.

This angle between the reference region and the body of the dissector may be determined in a number of ways. When the surfaces are flat, the determination of the relative angular position is quite clear as shown in the figures. When the reference region is a curved surface or one or more dimples or protuberances the angular relationship may be defined, for example, by determining the angle between two planes that best approximate reference region and the dissector surfaces.

Inner surface (274) and outer surface (273) generally converge at dissector tip (280). The profile of these converging dissector surfaces are created by grinding, chemical etching, machining, or the like. The dissector tip (280) may be ground sharp, or may be left with a slight radius or even a blunt tip if desired. As will be described in more detail below, the pocketing tool of the present invention allows the use of a sharper dissector tip with less risk. The grind angle (210) between the inner surface (274) and the outer surface (273) must provide for enough material in the dissector region to impart the necessary structural rigidity as well as remaining sufficiently thin for insertion into a corneal incision. The grind angle (210) is typically between about 10° to about 50°, more preferably about 25° to about 35°, most preferably about 30°. In the side view illustrated in FIG. 5, the dissector (270) may have be formed with a full radius (310) as shown. A small perpendicular hook or protrusion in the direction that is to be separated may optionally be provided at the dissector tip.

To achieve the desired size, structural integrity, and biocompatibility required for proper operation in corneal surgery, the pocketing tool (100) is typically made from stainless steel or titanium, preferably anodized titanium. For the purposes of example only, the material thickness in the vicinity of the shaft (140) and reference region (220) is typically about 0.014 to 0.020 inches. The side view width (282) of the tip section (150) is typically constructed to be somewhat smaller than the width of the incision that will be used, typically less than about one-half of the width of the expected incision. For typical incisions in the range of about 1 mm to about 1.2 mm, the width (282) is preferably about 0.02 inches. The downward distance (284) from the reference region (220) to the dissector tip (280) is preferably constructed to coincide with the desired depth of the corneal pocket to be formed. If for example, a pocket is to be created at a depth of 0.018 inches from the surface of the cornea, then the instrument will be constructed with a downward distance (284) of about 0.018 inches.

Because many corneal surgery procedures are performed while looking through a microscope, and thus instrument access can be significantly limited, it may be desirable to provide a corneal pocketing tool which has a handle offset from the working plane of the dissector. This allows manipulation of the dissector portion of the pocketing tool within the incision primarily by rotation of the handle about its longitudinal axis.

In contrast to the in-line configuration discussed above with reference to FIGS. 3–5, FIG. 6 illustrates a corneal pocketing tool (400) having a handle (420) which is offset from the dissector (470), dissector tip (480), and reference region (485). In addition to the dissector (470) being offset from the longitudinal axis (405) of the handle (420), the dissector (470), dissector tip (480) and reference region (485) have been rotated approximately 90° about a vertical axis (403) from their orientation as illustrated with regards to the in-line configuration discussed above. The handle (420) is preferably knurled to provide optimum gripping and may include one or more flat or recessed sections (410)

The dissector (470), dissector tip (480) and reference region (485) are constructed in the same manner as described above. Reference region (485) may connect directly to the shaft (440) or may connect by way of a straight or curved support member, such as straight support (490). Support (490) has an inclination angle (455) relative to the reference region (485) and connects to shaft (440) at connecting angle (450).

The pocketing tool is typically constructed such that the support (490), inclination angle (455) and connecting angle (450) result in the dissector (480) being in the desired dissector angle (460) to the reference region (485). As noted above, the dissector angle (460) may be between about 30° and 150°, more preferably between about 60° to 100°, most preferably about 75°. The access angle (453) of the handle (420) relative to the vertical axis (403) may be any angle suitable to allow the surgeon to see and manipulate the corneal pocketing tool into the incision and to begin intrastromal separation. Preferably, access angle (453) is less than about 90°, more preferably about 70° to about 90°.

Figure 6:
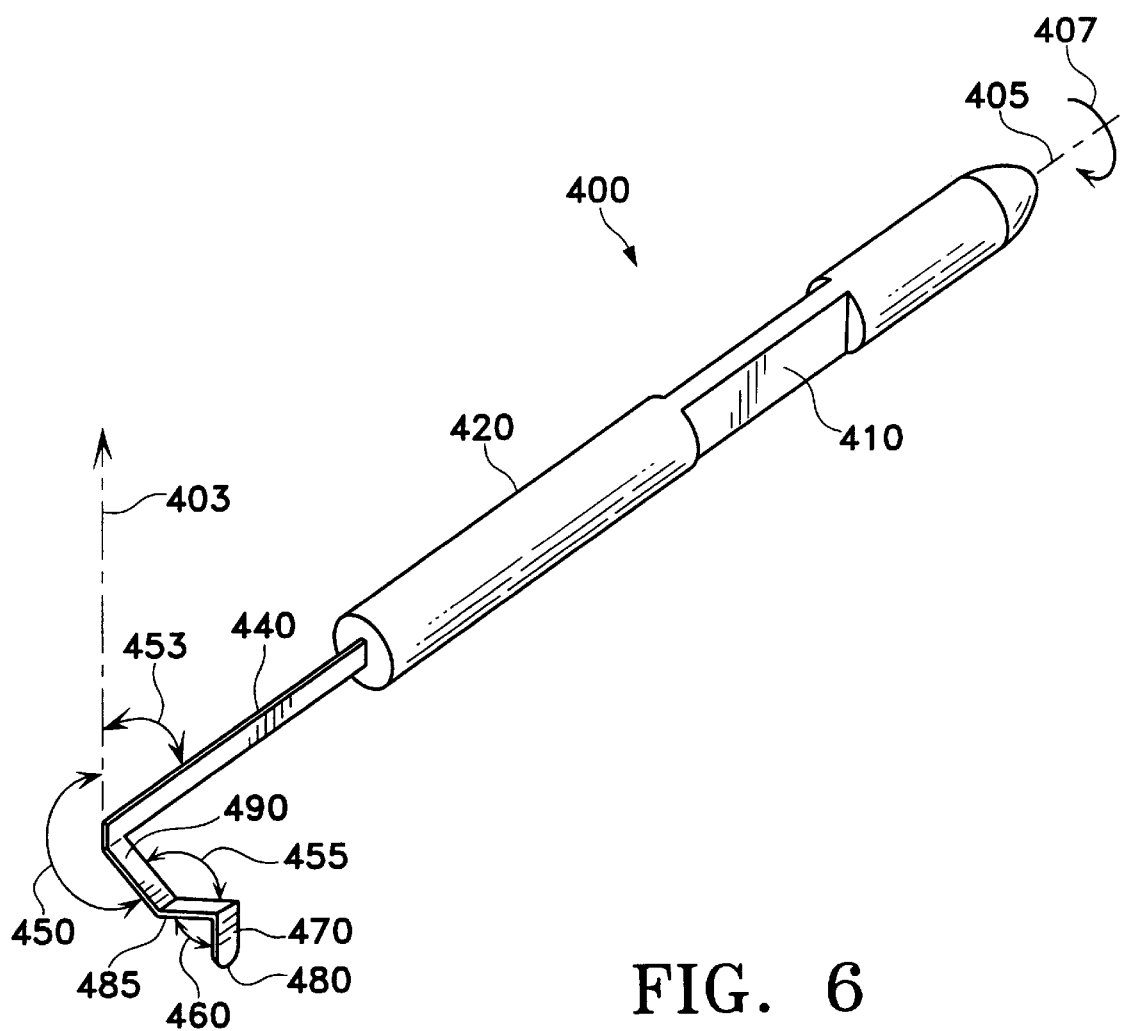
FIG. 6 is a perspective view of a pocketing tool having an offset handle.

Depending on the position of the incision in the cornea, the direction in which pocketing is to occur, whether it is the patient's left or right eye, and the positioning of other surgical instruments, it may be desirous to have an opposite-handed offset to that shown in FIG. 6. The principles described above apply equally well to a pocketing tool having an oppositely-handed offset.

To form a pocket or separation between the stromal layers of the cornea, the pocketing tool is inserted into a partial depth incision (610) as shown in FIG. 9. The partial depth incision (610) may be of any type or orientation from which intrastromal pocketing is to begin. The incision may be a circumferential type incision (510) for forming a radial pocket in the cornea 500 as illustrated in FIG. 7 or may be a radial type incision (550) for circumferential pocketing, for example, to form an intrastromal channel (560) as illustrated in FIG. 8. Preferably, the incision is made to the depth at which it is desired to create an intrastromal pocket.

The dissector (270) of the corneal pocketing tool is advanced into the incision (610) until reference region (220) comes into contact with the surface (605) of the cornea (620). The relatively large contact area of the reference region (220) ensures that there will be no significant damage to the corneal tissue as the surgeon applies the downward pressure necessary for insertion of the dissector (270) into the incision (610). The downward pressure applied to the corneal pocketing tool by the surgeon is absorbed by the reference region (220) rather than by the dissector tip (280) against the bottom of the incision. For this reason, the dissecting tip may be relatively sharp to facilitate pocketing, without risk to the surrounding tissue.

Because the distance from the reference region (220) to the dissector tip (280) corresponds to the desired depth for corneal pocketing (and coincidentally with the bottom of the partial depth incision), once the surgeon appreciates the tactile indication that the reference region (220) is in contact with the corneal surface (605) it is known that the dissector tip (280) is at the proper depth below the corneal surface (605). Thus, the surgeon is not required to use the dissecting tip to feel for the bottom of the incision, but instead proper depth of the dissecting tip is indicated by the resistance to further advancement of the reference region (220) against the corneal surface (605). This provides the surgeon with greatly improved tactile feedback that the instrument is fully inserted and reduces the risks of tissue damage or separating the tissue at an incorrect depth.

With the dissector 270 in place within the incision (610) as shown in FIG. 9, an intrastromal separation or pocket is initiated simply by pivoting or rotating the instrument in the direction indicated by the arrow (640). This allows the dissector (270) and dissecting tip (280) to rotate about the radius (272), forcing the stromal layers to delaminate by operation of the dissecting tip (280) at the proper depth below the corneal surface (605). The amount of rotation required is typically in the range of 10° to 90°, preferably around 45°.

As the instrument is rotated, the depth of the dissecting tip remains controlled in part by the reference region (220) as it rotates about radius (272), and a separation or pocket (630) is created. This rotational movement about the transition between the reference region (220) and the dissector (270) results at first in motion predominantly parallel to the corneal surface (605) and then begins to lift the separated tissue as rotation is furthered. If the width of the incision (610) is greater than the width of the dissector (270), it may be desirable to maneuver the dissector across the width of the incision either while holding the dissector (270) in the rotated position or by releasing and repositioning the dissector (270) to a new position along the width of the incision (610).

The rotation of the dissector (270) about radius (272) is ultimately accomplished by manipulation of the handle of the corneal pocketing tool. When the corneal pocketing tool has an in-line configuration, as illustrated in FIG. 3, the handle is maneuvered in the direction indicated by the arrow (107). For the offset corneal pocketing tool (400) illustrated in FIG. 6, the instrument requires rotational manipulation about the longitudinal axis similar to that indicated by the arrow (407). In this case, the space requirements to facilitate the overall displacement of the handle is considerably less than that of the in-line configuration.

Once the desired separation or pocket has been started using the present invention, various other instruments may then be inserted through the incision to enlarge or otherwise modify the pocket. For example, a larger pocket or channel may be created using a stromal spreader or various arcuate channeling tools inserted through the incision and into the initial pocket formed by the corneal pocketing tool described above.

All references cited above are hereby incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

We claim as our invention:

1. A surgical instrument comprising a reference region adapted to contact an anterior surface of a cornea and a dissector having a tip with a leading edge forming an end of said tip, said dissector and said reference region being oriented at an angle of less than about 110 degrees to each other, wherein said surgical is configured to separate the lamella of said cornea.

2. The surgical instrument of claim 1 wherein said angle is between about 60 degrees to about 100 degrees.

3. The surgical instrument of claim 1 wherein said angle is less than about 90 degrees.

4. The surgical instrument of claim 3 wherein said angle is about 75 degrees.

5. The surgical instrument of claim 1 wherein said reference region comprises a substantially planar surface.

6. The surgical instrument of claim 1 wherein said reference region comprises a curved surface having a radius of curvature between about 6 mm to about 10 mm.

7. The surgical instrument of claim 1, wherein said reference region and said dissector converge at a radius.

8. The surgical instrument of claim 1, further comprising an elongate handle connected to said reference region.

9. A surgical instrument comprising a reference surface and a dissector configured to separate the lamella of a cornea at the base of a partial-depth incision such that said dissector is positioned at an angle relative to said reference surface such that the free advancement of said dissector into said incision is prevented by contact of said reference surface against said cornea.

10. A surgical instrument comprising a reference region, a tip section and a handle section, said tip section having a dissector configured to separate lamellar tissue and to enter a partial-depth incision in a cornea to a dept of about 0.018 inches as limited by a reference region adapted to rest against the surface of the cornea.

11. The surgical instrument of claim 10, wherein said dissector and said reference region have a common intersection and whereby rotation of said handle causes said tip section to pivot about a point near said intersection.

12. The surgical instrument of claim 10 wherein said dissector is at an angle of less than about 110° to said reference region.

13. The surgical instrument of claim 11, wherein said intersection is a radiused surface connecting said reference region to said dissector.

14. A method of creating an intralamellar pocket at the base of a partial-depth corneal incision comprising the steps of
   (a) inserting a dissector of an instrument having a reference surface in angular relation to said dissector into said incision until the reference surface contacts the surface of the cornea; and
   (b) rotating the instrument about the vertex of the intersection of the reference surface and the dissector, whereby the distal dissecting tip is caused to separate the lamella of the cornea.

15. The instrument of claim 1 wherein said leading edge has a shape selected from rounded shapes and flattened shapes.

16. The instrument of claim 1 wherein said tip has a profile at least substantially perpendicular to said leading edge, said profile defining an angle between about 10° to about 50°.

17. The instrument of claim 16 wherein said profile defines an angle between about 25° and about 35°.

18. The instrument of claim 1 wherein said dissector tip is blunt.

19. The instrument of claim 9 wherein said dissector has an end with a leading edge having a shape selected from rounded shapes and flattened shapes.

20. The instrument of claim 19 wherein said end has a profile at least substantially perpendicular to said leading edge, wherein said profile defines an angle between about 10° to about 50°.

21. The instrument of claim 20 wherein said profile defines an angle between about 25° and about 35°.

22. The instrument of claim 1 wherein said tip has a section of constant width.

23. The instrument of claim 22 where said width is about 0.02 inches.

* * * * *